US00PP13349P2

(12) United States Plant Patent
van Rijn

(10) Patent No.: US PP13,349 P2
(45) Date of Patent: Dec. 10, 2002

(54) ANTHURIUM PLANT NAMED 'FRESH LOVE'

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 09/968,325

(22) Filed: Sep. 30, 2001

(51) Int. Cl.[7] ..... A01H 5/00
(52) U.S. Cl. ..... Plt./365

(58) Field of Search ..... Plt./366, 365

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Anthurium plant named 'Fresh Love', characterized by its upright and somewhat outwardly spreading plant habit; freely clumping growth habit; durable dark green leaves; white and green-colored spathes with light orange-colored spadices that are positioned above and beyond the foliage on strong and erect scapes; freely flowering habit; and good inflorescence longevity.

2 Drawing Sheets

BOTANICAL CLASSIFICATION

*Anthurium andreanum.*

VARIETY DENOMINATION

'Fresh Love'.

BACKGROUND OF THE INVENTION

The present invention relates to a new and distinct cultivar of Anthurium plant, botanically known as *Anthurium andreanum,* and hereinafter referred to by the name 'Fresh Love'.

The new Anthurium is a product of a planned breeding program conducted by the Inventor in Schipluiden, The Netherlands. The objectice of the program is to create and develop new freely clumping and freely flowering Anthurium cultivars with strong roots, dark green leaves, attractive spathe color, and good inflorescence longevity.

The new Anthurium originated from a cross by the Inventor on or about Jul. 24, 1997 of the Inventor's proprietary *Anthurium andreanum* selcetion code number 97-015 as the female, or seed, parent with the Inventor's proprietary *Anthurium andreanum* selection code number 97-010 as the male, or pollen, parent. The cultivar Fresh Love was discovered and selected by the Inventor as a plant within the progeny of the stated cross in a controlled environment in Schipluiden, The Netherlands in 1999.

Asexual propagation of the new cultivar by meristem culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Fresh Love. These characteristics in combination distinguish 'Fresh Love' as a new and distinct cultivar:

1. Upright and somewhat outwardly spreading plant habit.
2. Freely clumping growth habit.
3. Durable dark green leaves.
4. White and green-colored spathes with light orange-colored spadices that are positioned above and beyond the foliage on strong and erect scapes.
5. Freely flowering habit.
6. Good inflorescence longevity.

Plants of the new Anthurium can be compared to plants of the female parent, the selection 97-015. In side-by-side comparisons conducted in Schipluiden, The Netherlands, plants of the new Anthurium differed from plants of the selection 97-015 in the following characteristics:

1. Plants of the new Anthurium had flatter spathes than plants of the selection 97-015.
2. Plants of the new Anthurium flowered earlier than plants of the selection 97-015.
3. Spathe color of plants of the new Anthuriums was white and green whereas spathe color of plants of the selection 97-015 was white and pink.

Plants of the new Anthurium can be compared to plants of the male parent, the selection 97-010. In side-by-side comparisons conducted in Schipluiden, The Netherlands, plants of the new Anthurium differed from plants of the selection 97-010 in the following characteristics:

1. Plants of the new Anthurium had smaller leaves than plants of the selection 97-010.
2. Plants of the new Anthurium had smaller spathes than plants of the selection 97-010.
3. Spathe color of plants of the new Anthurium was not as pure white as spathe color of plants of the selection 97-010.

Plants of the new Anthurium can also be compared to plants of the cultivar Red Love, disclosed in U.S. Plant Pat. No. 11,005. In side-by-side comparisons conducted in Schipluiden, The Netherlands, plants of the new Anthurium differed from plants of the cultivar Red Love in the following characteristics:

1. Plants of the new Anthurium had shorter leaves than plants of the cultivar Red Love.

2. Plants of the new Anthurium had flatter spathes than plants of the cultivar Red Love.

3. Spathe color of plants of the new Anthurium were white and green whereas spathe color of plants of the cultivar Red Love were red.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar Fresh Love that was about two years old.

The photograph at the top of the second sheet comprises a close-up view of a typical inflorescence of 'Fresh Love'.

The photograph at the bottom of the second sheet comprises a close-up view of the upper surface of a typical mature leaf of 'Fresh Love'.

DETAILED BOTANICAL DESCRIPTION

In the following description, color references are made to The Royal Horticultural Society Colour Chart, 1995 edition, except where general terms of ordinary dictionary significance are used. The following observations and measurements describe two-year old plants grown in 17-cm containers in Schipluiden, The Netherlands, in a glass greenhouse with an average day temperature of 25° C. and an average night temperature of 19° C.

Botanical classification: *Anthurium andreanum* cultivar Fresh Love.

Parentage:

*Female parent.*—Inventor's proprietary *Anthurium andreanum* selection code number 97-015, not patented.

*Male parent.*—Inventor's proprietary *Anthurium andreanum* selection code number 97-010, not patented.

Propagation:

*Method.*—By meristem culture.

*Time to develop roots on a meristem-cultured plant.*—Summer: About 70 days at 24° C. Winter: About 84 days at 21° C.

*Root description.*—Strong fleshy roots.

Plant description:

*Plant shape.*—Upright and somewhat outwardly spreading plant habit, inverted triangle, symmetrical.

*Growth habit.*—Freely clumping, bushy and dense growth habit. Appropriate for 17 to 35-cm containers. Vigorous.

*Plant height.*—About 60 to 80 cm.

*Plant diameter or spread.*—About 90 cm.

*Crop time.*—About 10 months are usually required from planting of young plants to finished plants in a 17-cm container.

*Foliage description.*—Quantity per plant: About 100. Length: About 10 to 15 cm. Width: About 8 to 12 cm. Shape: Roughly cordate. Apex: Cuspidate. Base: Auriculate, not overlapping lobes. Margin: Entire. Texture: Leathery; glabrous. Venation pattern: Pinnate. Color: Young leaves, upper surface: 147A. Young leaves, lower surface: Between 143A and 146A. Mature leaves, upper surface: Closest to 147A. Mature leaves, lower surface: Between 144A and 146A. Venation, upper surface: 144A. Venation, lower surface: 145A. Petiole: Length: About 25 to 35 cm. Color: 144A. Geniculum length: About 1 to 2 cm. Geniculum color: 144A.

Inflorescence description:

*Inflorescence arrangement.*—Spathes with spadices held above and beyond the foliage. Flowering structures arise from leaf axils. Freely and continuous flowering year-round; typically more than 15 inflorescences per plant at one time.

*Inflorescence longevity.*—Inflorescences last about six weeks under winter conditions and about three months under summer conditions; persistent.

*Spathe.*—Length: About 7 to 10 cm. Width: About 10 to 13 cm. Shape: Broadly cordate. Apex: Cuspidate. Base: Truncate with auriculate tendencies. Margin: Entire. Texture: Leathery; glabrous; slight blistering. Color: When opening, front and back surfaces: Center, 155C; towards lateral margins, 137A to 141A; glossy. Fully developed, front surface: Center, 155C; towards lateral margins, 143A; glossy. Fully opened, back surface: Center, 155C; towards lateral margins, 143C; glossy.

*Spadix.*—Length: About 5 to 7 cm. Diameter: About 1 cm. Shape: Columnar. Cross section: Rounded. Longitudinal axis: Erect. Color: Immature: 31B. Mature: 29C.

*Flowers.*—Quantity per spadix: Numerous, about 200. Shape: Rounded. Diameter: About 1 mm, maximum.

*Reproductive organs.*—Androecium: Pollen color: Close to 158B. Gynoecium: Stigma shape: Ovoid.

*Scape.*—Length: About 35 to 40 cm. Aspect: Strong and erect. Color: 151D.

*Seed/fruit.*—Seed/fruit development on plants of the new Anthurium has not been observed to date.

Disease/pest resistance: Under commercial conditions, plants of the new Anthurium have not been observed to be risistant to pathogens or pests common to Anthurium.

It is claimed:

1. A new and distinct cultivar of Anthurium plant named 'Fresh Love', as illustrated and described.

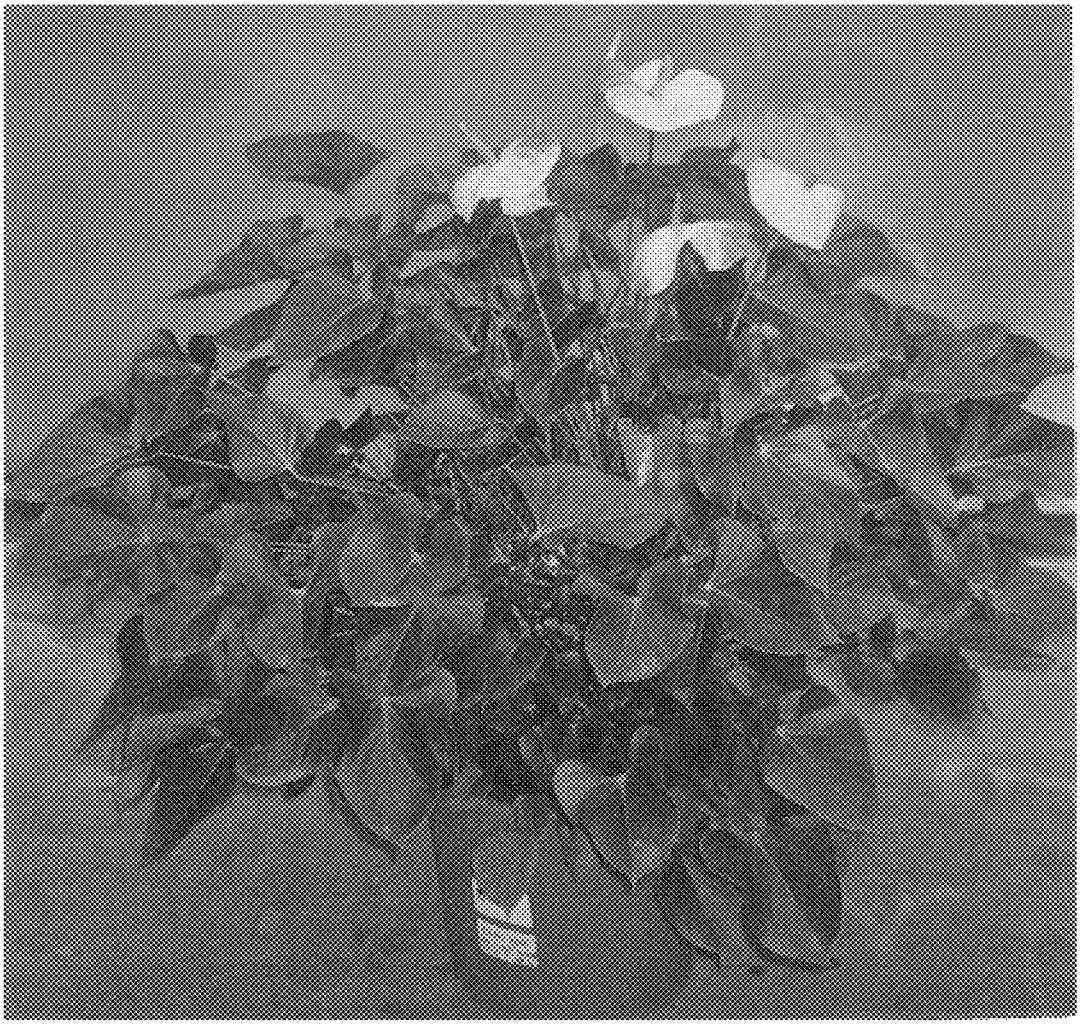

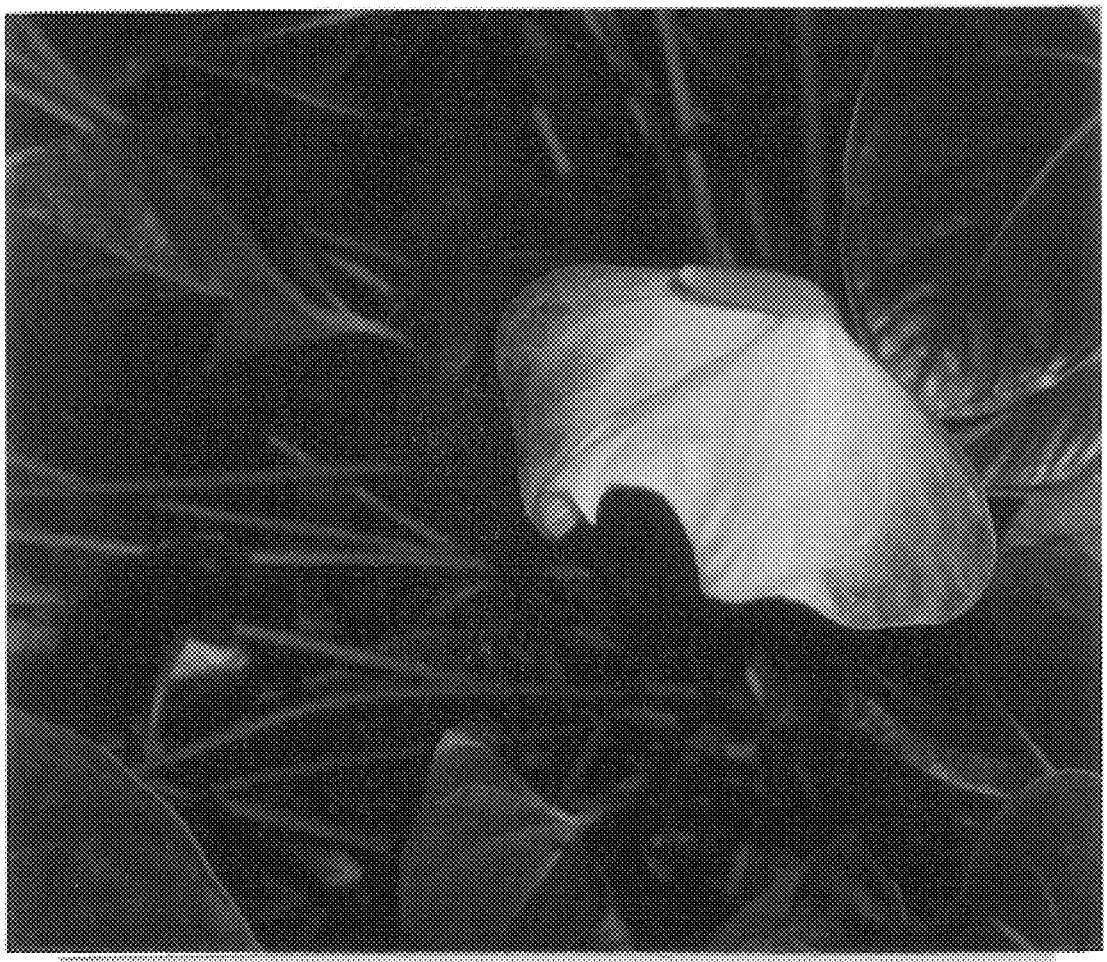
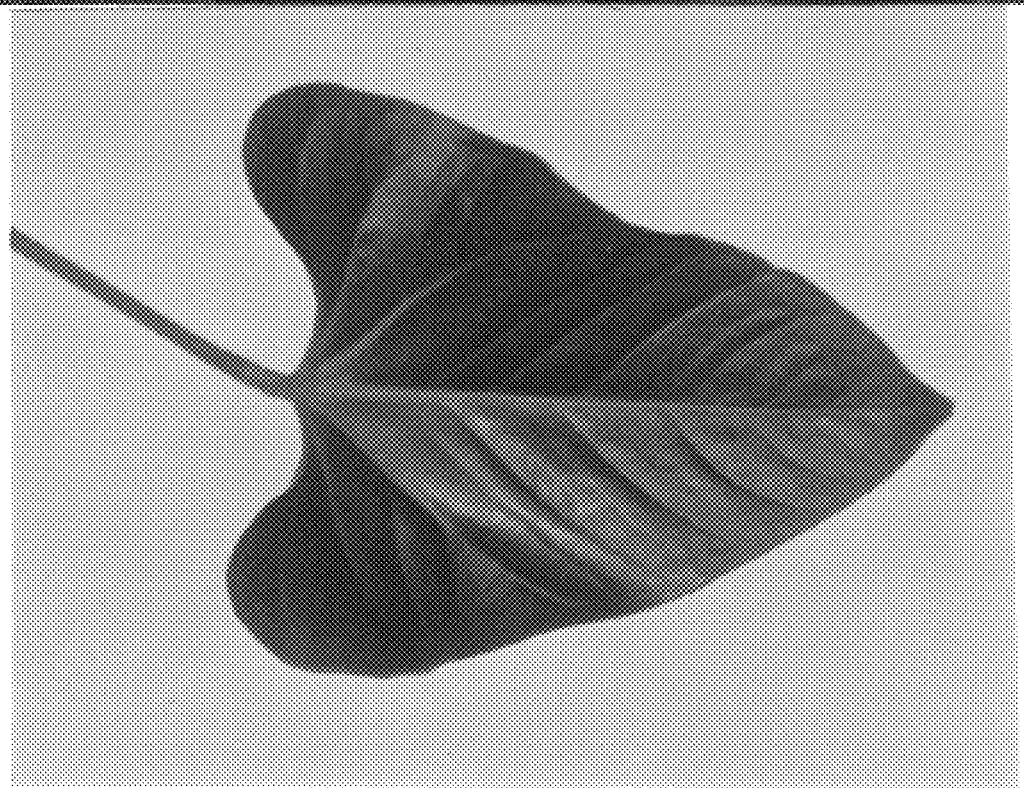

* * * * *